United States Patent [19]

Biermaier

[11] Patent Number: 5,288,467
[45] Date of Patent: Feb. 22, 1994

[54] CLEANING AND DISINFECTING MACHINE FOR MEDICAL EQUIPMENT AND INSTRUMENTS, ANESTHETIC TUBES, CATHETERS, AND ENDOSCOPES

[76] Inventor: Hans Biermaier, Winterbruckenweg 30, 8904 Friedberg/Derching, Fed. Rep. of Germany

[21] Appl. No.: 898,849

[22] Filed: Jun. 15, 1992

Related U.S. Application Data

[63] Continuation-in-part of Ser. No. 646,526, Jan. 25, 1991, abandoned, which is a continuation of Ser. No. 362,149, Jun. 6, 1989, abandoned.

[30] Foreign Application Priority Data

Jun. 6, 1988 [DE] Fed. Rep. of Germany ....... 3819257

[51] Int. Cl.$^5$ ............................ A61L 2/24; A61L 2/18
[52] U.S. Cl. .................................... 422/116; 422/293; 422/297; 422/905; 134/170
[58] Field of Search ............... 134/166 C, 169 C, 170, 134/200, 166 R; 422/116, 295, 297, 300, 292, 905, 293

[56] References Cited

U.S. PATENT DOCUMENTS

| | | | |
|---|---|---|---|
| 4,064,886 | 12/1977 | Heckele | 134/169 C X |
| 4,281,674 | 8/1981 | Tanaka et al. | 134/170 X |
| 4,299,244 | 11/1981 | Hirai | 134/170 X |
| 4,526,622 | 7/1985 | Takamura et al. | 134/21 |
| 4,526,623 | 7/1985 | Ishii et al. | 134/21 |
| 4,579,597 | 4/1986 | Sasa et al. | 134/21 |
| 4,731,222 | 3/1988 | Kralovic et al. | 422/292 X |
| 4,763,678 | 8/1988 | Ott | 134/169 C X |
| 5,090,433 | 2/1992 | Kamaga | 134/169 C |

FOREIGN PATENT DOCUMENTS 0345713 12/1989 European Pat. Off. .
3710517 10/1988 Fed. Rep. of Germany .

Primary Examiner—James C. Housel
Assistant Examiner—Jeffrey R. Snay
Attorney, Agent, or Firm—Cushman, Darby & Cushman

[57] ABSTRACT

A cleaning and disinfecting apparatus for medical equipment and instruments is provided. The apparatus includes at least one feed line constructed so as to be coupled for the supply of cleansing liquid and at least one outlet line for the discharge of spent cleansing liquid. A transportation and cleaning vessel is further provided which receives the articles to be cleaned and is adapted to be placed in and taken out of the apparatus. The vessel has at least one inlet and at least one outlet, the inlet being adapted to be connected to the feed line and the outlet being adapted for coupling to the discharge line. The inlets and outlets can be closed by non-return flaps on valves which are in closed position when inoperative and are opened by pressurized fluid.

7 Claims, 5 Drawing Sheets

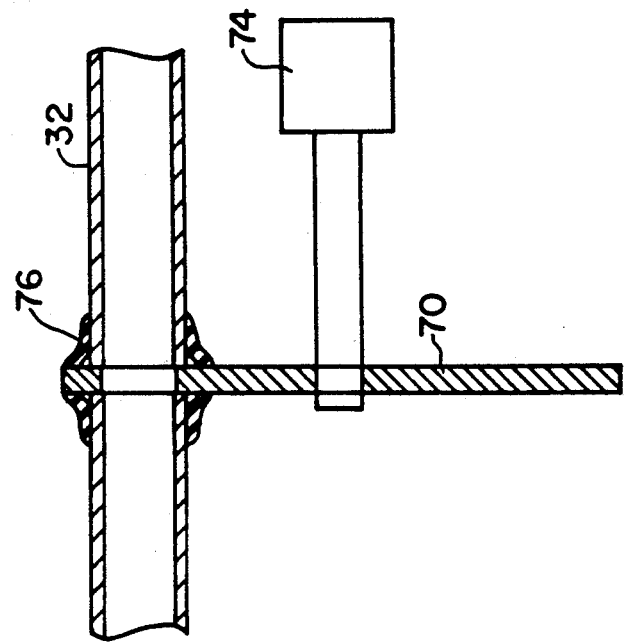
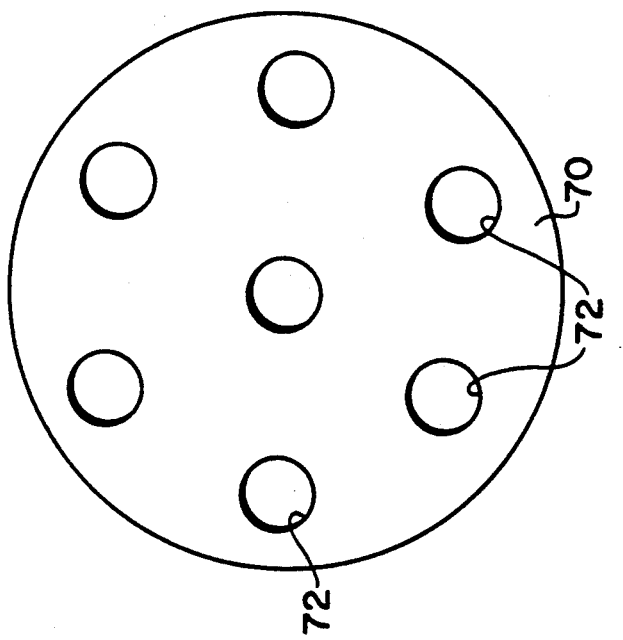

CLEANING AND DISINFECTING MACHINE FOR MEDICAL EQUIPMENT AND INSTRUMENTS, ANESTHETIC TUBES, CATHETERS, AND ENDOSCOPES

This is a continuation-in-part of application Ser. No. 07/646,526 filed Jan. 25, 1991, now abandoned, which was a continuation of application Ser. No. 07/362,149 filed Jun. 6, 1989, now abandoned.

BACKGROUND OF THE INVENTION

1. Field of the Invention

The instant invention relates to a cleaning and disinfecting apparatus for medical equipment and instruments, especially for anesthetic tubes, catheters, and endoscopes comprising at least one feed line adapted to be coupled for the supply of cleansing liquid and at least one outlet line for the discharge of spent cleansing liquid.

2. Description of the Related Art

A machine or apparatus of the above mentioned kind, referred to also as a disinfecting —rinsing apparatus, is known from DE 37 10 517 A1 which is not a prior publication. In that case an endoscope is introduced partly into a tube inside the washing apparatus and a cleansing liquid is passed under pressure through the tube, whereby the cleaning conditions are improved. The head of the endoscope which should not get into contact with the cleansing liquid is held in a molded member which is largely liquid tight with respect to the washing space. In addition pressurized air is applied to the molded member so as to prevent the entry of cleansing liquid.

Endoscopes are cleaned very well with the known machine. However, the transportation of cleaned and disinfected endoscopes within the patient rooms still causes problems. When endoscopes are taken out of the disinfecting washer they are no longer protected from the moment against any renewed contamination. Still more problematic is the transportation of used instruments, in other words devices that are contaminated and must be brought to the disinfecting machine. While on their way, they pose a risk of contamination to the whole surroundings, including patients and staff.

SUMMARY OF THE INVENTION

It is, therefore, an object of the invention to improve a machine of the kind specified initially such that the articles to be cleaned neither can be contaminated themselves nor can they contaminate something else while on their way to and from the machine.

This object is met with a machine of the generic kind in question by having a transportation and cleaning vessel which receives the articles and is adapted to be placed in and taken out of the machine. The vessel has an opening for the loading and unloading of articles to be cleaned which opening can be closed tightly and the vessel has at least one inlet and at least one outlet, the inlet being adapted to be connected to the feed line and the outlet adapted for coupling to the discharge line. Both inlets and outlets can be closed by non-return flaps or valves which are in closed position when inoperative and are opened by pressurized fluid.

Advantageous modifications and further developments of the invention may be gathered from the subclaims.

The basic concept of the invention resides in conveying the articles that are to be cleaned or have been cleaned in a closed container which then is connected to the apparatus during the washing and disinfecting procedure. Apart from the short duration of actual use with a patient, the medical equipment thus always remains inside said vessel, particularly also during the cleaning and disinfecting. With the cleaning completed, the entire vessel is removed from the machine and brought to the patient. Therefore, the medical equipment, while on its way, is absolutely protected from any contamination and also can be stored for a longer period of time in that way. Vice versa, instruments that have become contaminated from use are immediately returned into the vessel when they are no longer used. The vessel is closed and then moved back to the disinfecting and cleaning machine. On the way back consequently the contaminated articles cannot contaminate the environment.

The vessels themselves are connected by means of couplings, preferably quick-acting couplings establishing communication with the washing system which comprises the feeding and discharging of cleansing liquid and disinfectant. Communication may be established also with a compressed air system and/or a vacuum system which may be needed during certain phases of the cleaning process.

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWING

The invention will be described further, by way of examples, with reference to the accompanying drawings, in which the most important component parts of the cleaning and disinfecting machine of the invention are shown.

FIGS. 2 and 3 show a transporting, storing and cleaning vessel, which receives articles to be cleaned and sterilized, wherein FIG. 2 shows a pressure chamber of said vessel in a closed position and FIG. 3 shows the pressure chamber in an opened position;

FIG. 4 shows a detail of the pressure chamber with an endoscope to be cleaned placed in;

FIG. 5 is a plan view of a rotary disc of an alternate valve which may be used in the apparatus of FIG. 1;

FIG. 6 is an elevational view partly in cross-section of a valve which may be incorporated in the apparatus of FIG. 1.

DESCRIPTION OF THE PRESENTLY PREFERRED EXEMPLARY EMBODIMENTS

Figure 1:
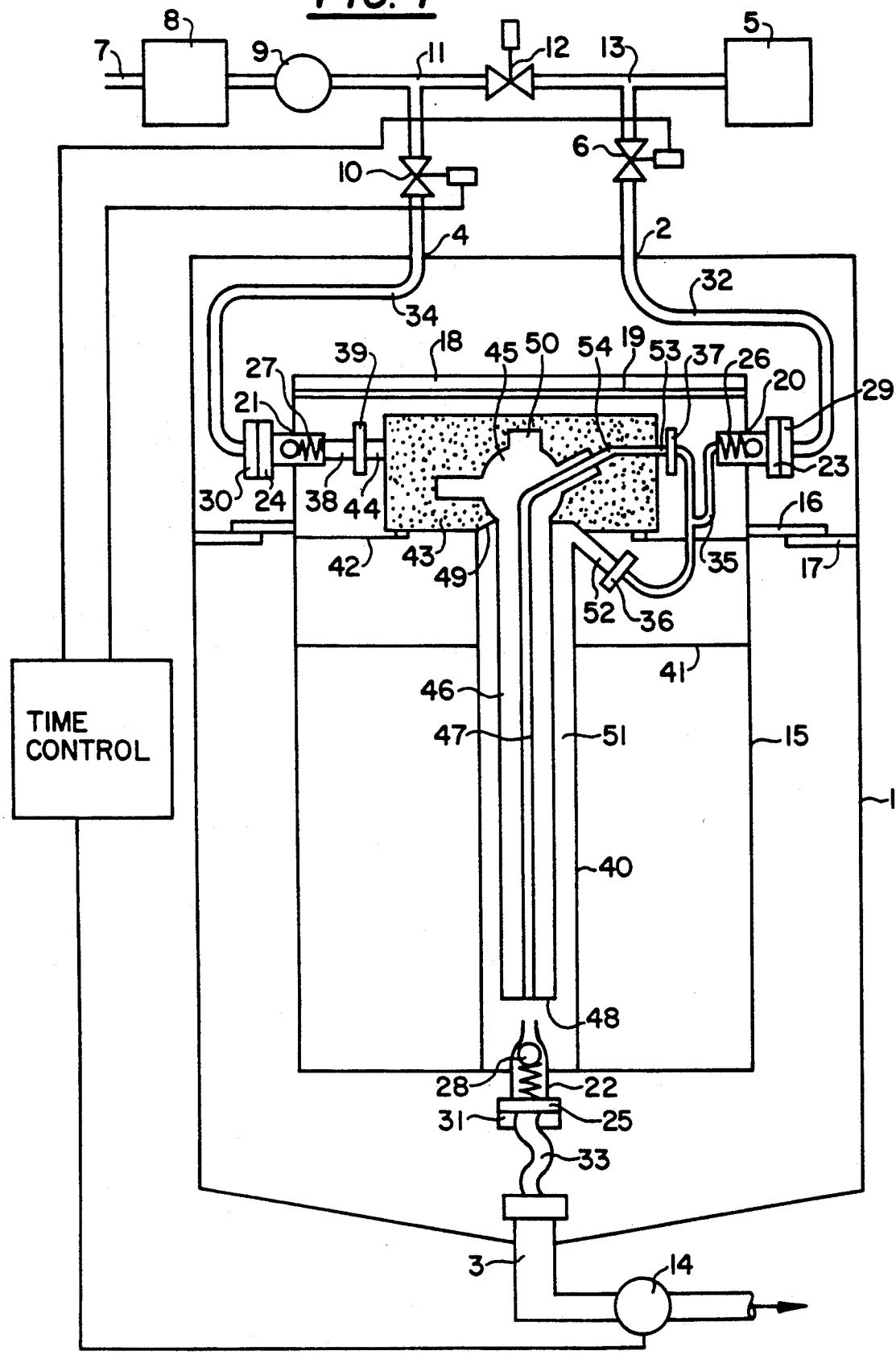
FIG. 1 shows diagrammatically the apparatus of the invention.

A washing space 1 of a cleaning and disinfecting machine comprises at least one feed line 2 for the supply of cleansing and disinfecting liquids, at least one outlet or discharge line 3 through which all the liquids are removed from the washing space, and a compressed air supply line 4 through which the sterile filtered pressurized air is introduced into the washing space 1.

A supply system for cleansing and disinfecting liquids (such as water with an addition of detergent, liquid disinfectant, etc.) is indicated by reference numeral 5. This system supplies the liquids mentioned through a magnetic valve 6 to the feed line 2. The compressed air system begins with an air inlet 7 passing air through a sterile filter 8 by means of a pump 9 and then on through a magnetic valve 10 to the compressed air supply line 4. A T-connector 11 disposed between the pump 9 and the magnetic valve 10 can pass pressurized air through another magnetic valve 12 as well into the liquid system, more specifically to a T-connector 13 which establishes communication with the magnetic valve 6 and the feed line 2. Through this path compressed air can be introduced also into the liquid system, a circumstance which is especially important if residual water is to be blown out after the cleaning process. With endoscopes in particular which in part have narrow cavities of the kind of capillary tubes, any liquid which remains after cleaning can be removed only by pressurized air. The compressed air system moreover may be used for drying and sterilizing if the compressed air is heated.

A pump 14 is connected to the discharge line 3 and it may be left in operation for the whole time of the washing process, whereby a vacuum is produced to guarantee a constant pressure drop from top to bottom in the machine. In this way the necessary liquids are passed faster through the machine, providing improved cleaning efficiency.

In the interior of the washing space 1, a vessel 15 can be seen which has lateral support arms 16 to hold it on rails 17 and which contains the articles to be cleaned. The vessel 15 has a lid 18 which can be opened and which provides a tight seal for the vessel when closed. The sealing may be embodied by a rubber seal 19, for example. The lid may be designed as a hinged flap or screwed-on cover. The opening must be so big that it will be easy to place the material to be cleaned inside. In the embodiment shown the vessel 15 has three other apertures, namely one inlet 20 for cleansing liquid, one inlet 21 for compressed air, and one outlet 22. These three apertures may be designed as pipe nozzles at the outer ends of which there is a coupling each 23, 24 and 25, respectively, for the connection of pipes or conduits. The couplings may be simple plug-in couplings adapted to receive a flexible hose which is simply slid on. It is likewise possible to provide quick-acting couplings, such as bayonet-type couplings. Another possibility is to provide automatically engaging couplings which are mounted on the vessel in such manner that they establish automatic fluid communication with connections in the washing space when the vessel is pushed in. The three additional apertures 20, 21 and 22 in the vessel each are furnished with a non-return flap over valve 26, 27 and 28 respectively. Non-return valves 26 and 27 open in the incoming direction, while non-return valve 28 opens in the outgoing direction. These valves, unless pressured in the direction of passage, close automatically and, therefore, prevent any bacteria and the like from passing. This means that in particular during transportation all the valves are closed so that, with the lid 18 closed, the vessel is absolutely tight.

Lines 32, 34 and 33, respectively, are connected to the respective one of the three couplings 23, 24 and 25 by counter coupling members 29, 30 and 31, respectively. Line 32 carries the cleansing liquid to the vessel. Line 33 removes the spent cleansing liquid, and line 34 feeds the compressed air. In the embodiment shown, the lines 32, 33 and 34 are flexible hoses leading to different points inside the washing space so that vessels, containers, or cassettes of different sizes can be accommodated.

The interior of the vessel is adapted to the respective goods to be cleaned. For instance, various outlet nozzles may be provided for the cleansing liquid. Also, specific connections may be provided in particular for the cleaning of hoses and endoscopes. In the embodiment shown, the vessel 15 is designed for the cleaning of an endoscope.

To that end, the outlet of the non-return valve 26 is connected to a hose 35 which is divided into two branches ending by two couplings 36 and 37. Hereby the cleansing liquid is distributed along two paths as required for cleaning the interior operating channel and the outside of an endoscope. The outlet of non-return valve 27 is connected to a hose 38 which likewise terminates in a coupling 39. Finally, also the outlet of non-return valve 28 is connected to a coupling 25 adapted for connection to a coupling 31 of hose 33. For special adaptation to the cleaning of hoses and endoscopes a tube 40 is provided inside the vessel 15 to take up the hose of the endoscope. This tube 40 is supported by a retaining means 41 on the inner wall of the vessel. In consideration of the particular needs of endoscopes which have a "non-washable head" the tube opens at its top end into a space of sealing material 43 which is of porous nature and has a cavity adapted to the shape of the endoscope head 45. This porous sealing material 43 has a connecting piece 44 for compressed air to which the coupling 39 may be joined. Thus the porous sealing material can be pressurized so that the cleansing liquid will not reach the endoscope head 45.

A flexible endoscope tube 46 formed with an operating channel 47 in its interior has been slid into the tube 40, as seen in the drawing, and an intermediate space 51 is left open between the inner wall of the tube 40 and the endoscope tube 46. Moreover, the distal end 48 of the endoscope tube 46 is shorter than tube 40. At its upper end, the intermediate space 51 opens into an outlet connecting piece 52 to which the coupling 36 may be joined. The operating channel 47 communicates with the connecting piece 53 through a line 54 to be connected. The coupling 37 can be connected to the connecting piece 53. In this manner cleansing and disinfecting liquid can be introduced into the operating channel 47 and into the intermediate space 51. The pressurized liquid will flow through these spaces and is removed by the low pressure acting at the outlet valve 28. As the tube 40 is longer than the endoscope tube 46 there is, at the distal end 48 of the endoscope tube 46, an edge where flow is broken away so that the low pressure in the operating channel 47 and the intermediate space 51 is reinforced. Pressurization of the porous sealing material 43 by compressed air causes a pressurized space 49 to be formed at the inlet into the intermediate space 51 so that the cleansing liquid is subjected to the pressure of the compressed air in addition to its own pressure.

As the washing space of customary machines is of limited height, the tube 40, of course, may be given spiralling shape if very long hoses or endoscopes are to be cleaned.

Furthermore, of course, the inside of the vessel 15 is to be adapted to the specific requirements. For instance, to clean test tubes, bottles and the like a plurality of prong-like holding members with nozzles may be provided. It is likewise possible to lay pipe systems with cleaning nozzles in the interior of the vessel, just as may be required. Of course, it is likewise conceivable to introduce a plurality of vessels 15 at the same time into the machine. In this case, either a plurality of hoses must be provided for separate connection of each individual vessel or the vessels themselves may include additional pipe connections so that one vessel can be coupled to another whereby the communication required can be established. Of course, also the configuration or shape of the vessel can be devised as desired. In the embodiment shown, the vessel also might be embodied directly by the tube 40 and the sealing material 43 for the head of the endoscope. In that event the sealing material would have a tight outside coating, for instance of plastics and the housing thus formed would have to be designed for appropriate opening at the side. The only critical aspect is that the resulting container or vessel must be absolutely tight against contamination.

According to another modification of the invention, not illustrated in the drawing, the vessel 15 itself presents the washing space of the machine. In that case the machine comprises two modules, namely the exchangeable washing space (vessel) and the complete washing system including control units, pumps, heaters, monitors, and a drier-fan as well as the unit of the "washing compartment" to be coupled by quick-acting couplings and constituted by the vessel or vessels. Such an arrangement provides for better maintenance as there is total separation between parts not subject to wear and, therefore, not prone to repair, such as the washing compartment or vessel and those parts which do wear. Thus a machine can be produced which involves lower follow-up costs as the final user himself can replace the complete aggregate which is subject to wear.

Furthermore, it should be stressed at all the connections (cleaning system, compressed air system, and discharge system) are arranged in a manner which will cause all the agents (cleansing liquid, disinfecting liquid, compressed air) always to flow from top to bottom through the machine. On the one hand, that increases the flow velocity still further. On the other hand, less liquid remains behind in the machine. If indeed there should be any residual liquid, it will be blown out by switching compressed air into the cleaning system.

The constant provision of vacuum at the outlet end of the machine in addition offers the favorable opportunity of being able to meter the quantity of cleansing and disinfectant additives without having to provide a dosage pump. In cooperation with the timed control of magnetic valves this low pressure can suck the detergents to be added directly from a reservoir. Hereby the metering pumps can be dispensed with which are very susceptible to trouble anyway and usually quite inaccurate.

Finally, it should be observed that, although not presented in the drawing, means may be provided to wash the outside of the vessel. That can be done by additional nozzles which open into the washing space 1. Customary washing arms likewise may be provided. In certain cases washing arms of conventional kind may be used which rotate in the interior of the vessel.

Figure 2:
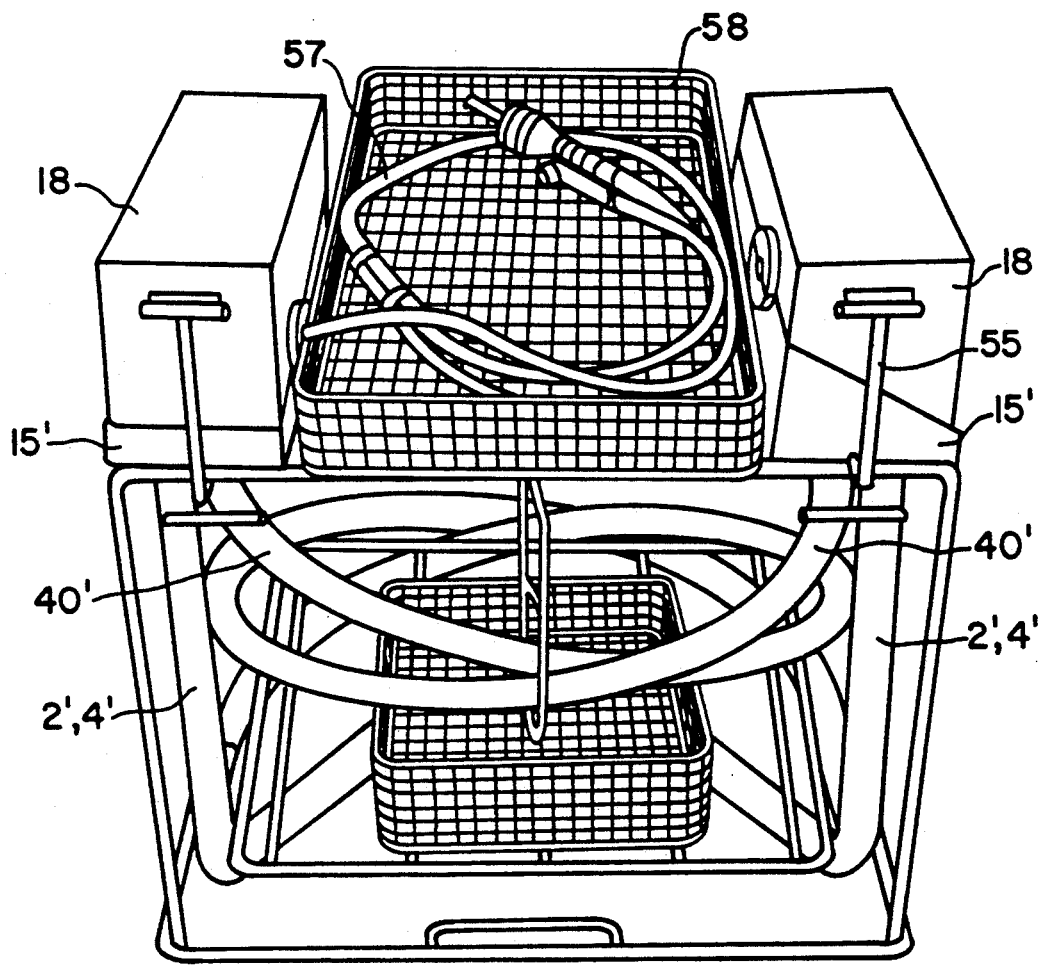
Figure 3:
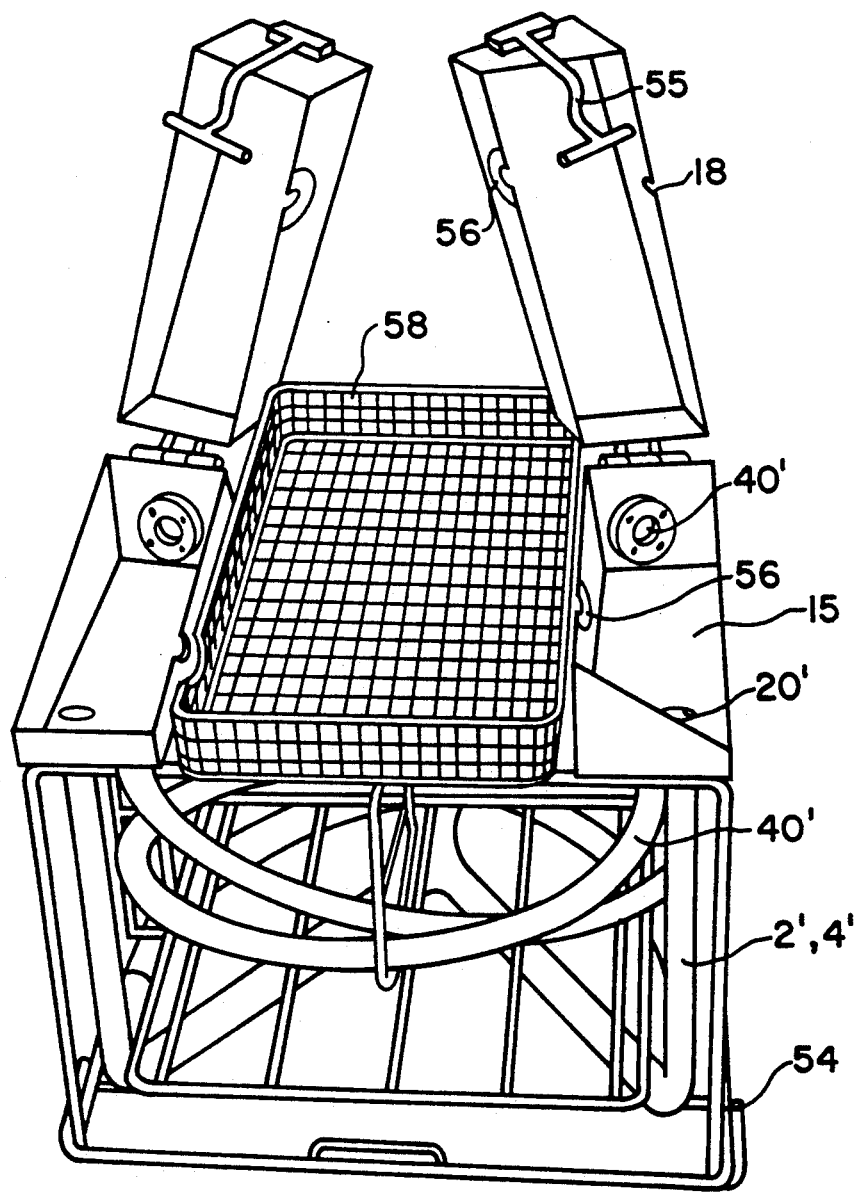

Reference is now made to FIGS. 2 and 3. The transporting storing and cleaning vessel, which is adapted to be placed in and taken out of a cleaning and disinfecting machine has a rack 54 which supports two similar pressure chambers 15' each having a lid 18, which can be opened and provide tight seal for the pressure chamber when closed. The lid is designed as a hinged flap having a handle 55 for locking the lid in a closed position. The pressure chamber 15' is adapted to receive the head 45' (FIG. 4) of an endoscope and has in the embodiment of FIGS. 2 and 3 three openings. The first opening 20' is a common inlet for cleansing and disinfecting fluid and/or compressed air.

The second opening of the pressure chamber is connected to the tube 40', which receives the endoscope tube 46' of the endoscope.

A third opening 56 of the pressure chamber 15'is adapted to be an outlet of the pressure chamber, where a control portion 57 of an endoscope can extend outside the pressure chamber. Nearby the third opening 56 is a basket 58, which receive the control portion 57.

The third opening 56 has a seal, which closes the pressure chamber tightly when the control portion 57 of the endoscope extends through said third opening 56.

Figure 4:
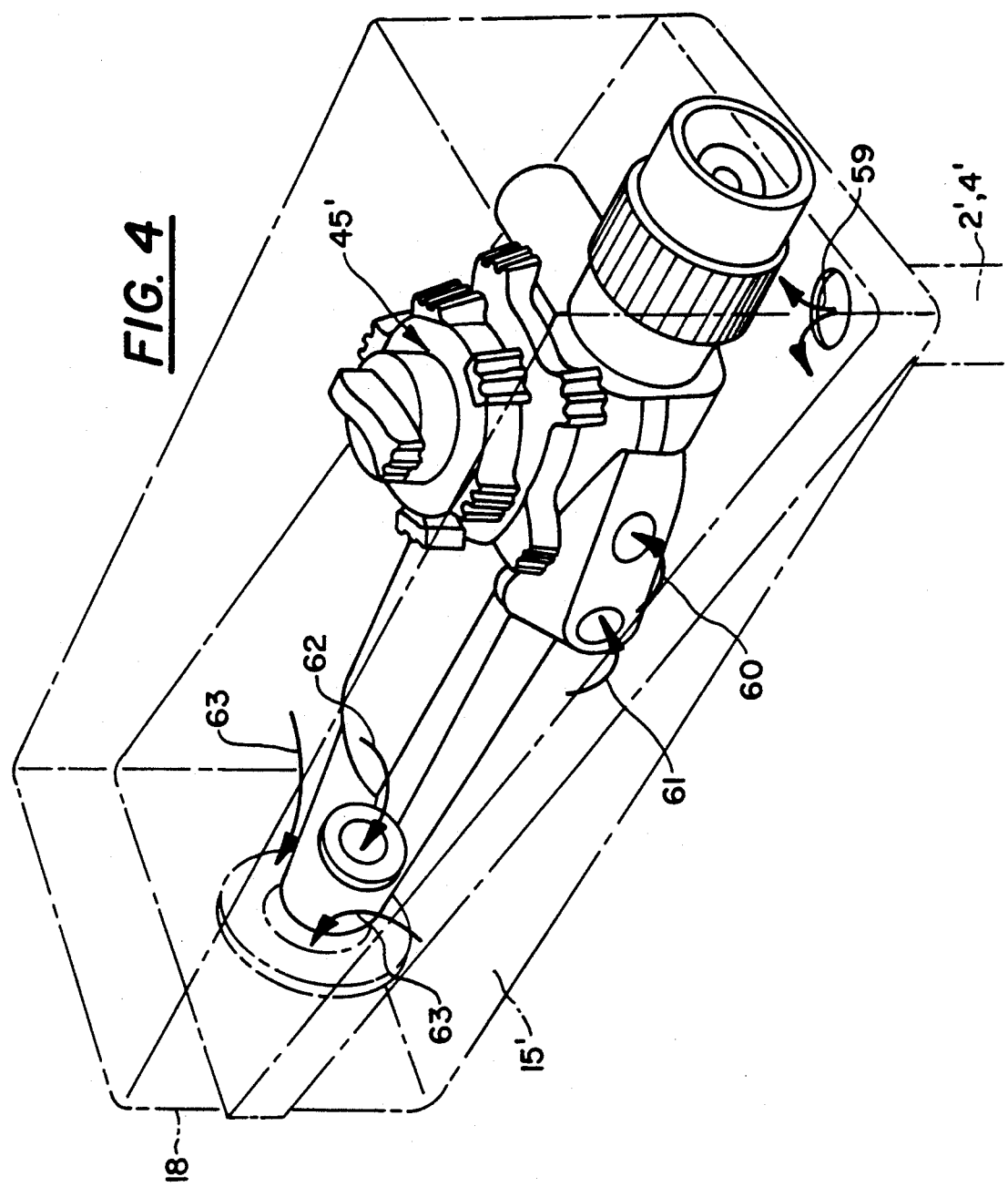

Reference is made to FIG. 4, where an endoscope head 45 is placed into the pressure chamber 15. Pressurized cleansing and disinfecting liquid is fed to the inside of the pressure chamber via the feed line 2 as shown by arrows 59. As known in the art the endoscope head has at least one, in practice several inlets to interior channels. The pressurized cleansing and sterilizing liquid and/or pressurized air flows into these openings as shown by the arrows 60, 61 and 62.

As shown in FIG. 4 the cleaning and sterilizing liquid and/or pressurized air from the pressure chamber is indicated by the arrows 63.

In accordance with a further aspect of the invention, a pressure oscillation is superimposed on the cleaning liquid to improve the cleaning effect thereof and to save cleansing fluid. More particularly, when a liquid having such an oscillation superimposed thereon contacts the article being cleaned, the oscillation energy helps to remove contaminates from the surface of the article. Any known oscillator which is capable of superimposing a mechanical oscillation on a fluid stream can be used in accordance with the invention to superimpose a pressure oscillation on the cleansing fluid. However, in practice, some limitations are required. For example, the oscillator must be capable of generating sufficient oscillation without being unduly large. Thus, for example, a piston pump, which delivers the liquid and which by its operation automatically superimposes a certain oscillation to the fluid stream would probably be inappropriate for the purposes of the invention because such a pump would have to be very great in size to provide for sufficient oscillation.

In accordance with the preferred embodiment the oscillation of the fluid stream is effected by superimposing pulses of pressurized air or gas on the fluid stream. To that end, three embodiments will be disclosed in particular.

In accordance with one embodiment of the invention, oscillation of the fluid stream is effected by opening and closing valve 12 (FIG. 1) with high frequency. Electromagnetically driven valves are known and are available on the market which have an upward frequency limit in the range of 10 to 100 kilo cycle/second and could be utilized for valve 12 if the valve is driven by an appropriate electrical oscillator. The pressurized air from pump 9 will act on the fluid from supply system 5 and, therefore, the fluid in line 32 will be a mixture of fluid and pressure air pulses and will therefore oscillate.

Substantially the same effect can be obtained by replacing the above mentioned valve with a motor driven rotary disk 70 having one or more holes 72. (FIGS. 5 and 6). The disk 70 is inserted into the line feeding pressurized air to line 32. When the disk is driven it interrupts the air stream periodically thereby superimposing a pressure oscillation onto the fluid. In the illustrated embodiment, a motor 74 rotates the rotary disk 70 so that the peripheral apertures 72 are sequentially aligned with a compressed air supply line. A seal or a gasket 76 which prevents escape of compressed air but allows rotation of the rotary disk 70 is provided at the juncture of the disk 70 and the supply line.

A third embodiment for imposing a pressure oscillation is to use a pressure pump having a rotary impeller, its vanes having supercritical form for providing a cavitation effect at the tip of the vanes when rotated. Such a pressure pump could be installed elsewhere in the feed system for the stream of cleaning fluid.

Generally, the cavitation effect occurs at any impeller which is misadapted for its intended purpose. As it is well known in the art, the vane of an impeller has one side of high pressure and another side of low pressure. If the low pressure is below a critical value then the liquid in this area reaches the pressure for vaportension. If this occurs, the fluid (like water) changes in state to become a gas and expands its volume. This change in state is very rapid, like a small explosion. As a result, a pressure wave runs from the impeller vane through the fluid.

Normally, for rotary pumps this cavitation effect should be avoided because the feeding rate is lowered. As is well known in the art, the cavitation effect depends on the following parameters: rotation speed of the vanes, form of the vanes and angle of pitch of the vanes. Of course, these parameters depend from one another. The simplest way to reach the cavitation effect in the present invention is to use a normal pump but drive it at a higher rotational speed than it is built for.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

What is claimed is:

1. A cleaning and sterilizing apparatus for medical equipment and instruments, including anesthetic tubes, catheters, and endoscopes, comprising:

a transporting, storing, and cleaning vessel which receives articles to be cleaned and sterilized; a feed line for supplying cleansing liquid to said vessel; a compressed air supply line; a cleansing liquid supply line for cleansing liquid under pressure; and an output line for discharging spent cleansing liquid from said vessel, wherein:

(a) said vessel is constructed so as to be placed in and removed from remaining components of the apparatus;

(b) said vessel consists of a pressure chamber and a tubular element which is in fluid communication with said pressure chamber;

(c) said pressure chamber has an opening for loading and unloading articles to be cleaned and means tightly closing said opening;

(d) said pressure chamber has an inlet having means for coupling to said feed line;

(e) said feed line has means for connecting to at least one of said compressed air supply line and said cleansing liquid supply line;

(f) said tubular element has an outlet having means for coupling to said outlet line for discharging spent cleansing liquid;

(g) said tubular element is constructed so as to define a vacuum system with respect to an inner passage of an article to be cleaned when liquid flows along a gap between an outside surface of the article and an inner wall of said tubular element;

(h) a time controlled magnetic valve is provided in each of the compressed air supply line and the cleansing liquid supply line, said magnetic valves being constructed so as to open and close a fluid path from a supply for pressurized cleansing liquid and a supply for pressurized air to said feed line, and (i) means for controlling said time controlled magnetic valves is provided to selectively meter at least one of liquid cleansing agents, and pressurized air into the vessel.

2. An apparatus according to claim 1, wherein said inlet is provided with a check valve which is normally biased to a closed position and is constructed so as to be opened by pressurized fluid.

3. An apparatus according to claim 1, wherein a check valve is defined at a distal end of said tubular element, said check valve being normally biased to a closed position and being constructed so as to be opened by pressurized fluid.

4. An apparatus according to claim 1, further comprising means for superimposing a pressure oscillation onto the stream of cleansing liquid flowing through the vessel, said superimposing means being constructed so as to superimpose pulses of pressurized gas onto said stream of cleansing liquid.

5. An apparatus according to claim 4, wherein said means for superimposing an oscillation comprises a shut-off valve provided in the compressed air supply line, wherein said compressed air supply line is in fluid communication with the cleansing liquid supply line and wherein said valve is driven with a high frequency.

6. An apparatus according to claim 4, wherein said means for superimposing an oscillation comprising a motor driven rotary disc inserted into the compressed air supply line and having at least one hole which opens the compressed air supply line when aligned with said line.

7. An apparatus according to claim 4, wherein said means for superimposing an oscillation comprises a pressure pump which is in fluid communication with the cleansing liquid supply line and having a rotary impeller, vanes of which have a supercritical form for providing a cavitation effect at the tips of the vanes when rotating with a supercritical speed.

* * * * *